United States Patent
Nyholt et al.

(10) Patent No.: US 8,408,065 B2
(45) Date of Patent: Apr. 2, 2013

(54) DRY-COUPLED PERMANENTLY INSTALLED ULTRASONIC SENSOR LINEAR ARRAY

(75) Inventors: John Nyholt, Seabrook, TX (US); Gary N. Langlois, Richland, WA (US)

(73) Assignee: BP Corporation North America Inc., Houston, TX (US)

( * ) Notice: Subject to any disclaimer, the term of this patent is extended or adjusted under 35 U.S.C. 154(b) by 751 days.

(21) Appl. No.: 12/406,619

(22) Filed: Mar. 18, 2009

(65) Prior Publication Data
US 2010/0236330 A1    Sep. 23, 2010

(51) Int. Cl.
*G01N 29/24*    (2006.01)

(52) U.S. Cl. ............................................. 73/644

(58) Field of Classification Search ............ 73/644, 73/609, 617, 632
See application file for complete search history.

(56) References Cited

U.S. PATENT DOCUMENTS

| | | | |
|---|---|---|---|
| 3,494,179 A * | 2/1970 | Brech | 73/627 |
| 4,881,409 A | 11/1989 | Roarty | 73/597 |
| 5,377,553 A | 1/1995 | Knepper, Jr. | 73/866.5 |
| 5,869,767 A | 2/1999 | Hayward et al. | 73/774 |
| 5,913,243 A | 6/1999 | Hopeck et al. | |
| 6,036,646 A * | 3/2000 | Barthe et al. | 600/459 |
| 6,120,452 A * | 9/2000 | Barthe et al. | 600/459 |
| 6,213,948 B1 * | 4/2001 | Barthe et al. | 600/445 |
| 6,745,628 B2 * | 6/2004 | Wunderer | 73/579 |
| 6,784,662 B2 * | 8/2004 | Schlicker et al. | 324/242 |
| 6,923,067 B2 * | 8/2005 | Coen et al. | 73/627 |
| 6,954,406 B2 | 10/2005 | Jones | 367/152 |
| 6,980,688 B2 * | 12/2005 | Wilk | 382/152 |
| 7,210,355 B2 | 5/2007 | Kawabata | 73/644 |
| 7,234,519 B2 | 6/2007 | Fripp et al. | 166/250.01 |
| 7,712,369 B2 * | 5/2010 | Georgeson | 73/632 |
| 2006/0010995 A1 | 1/2006 | Silverman et al. | 73/865.8 |

FOREIGN PATENT DOCUMENTS

| | | |
|---|---|---|
| EP | 1690604 A1 | 8/2006 |
| WO | 9924967 A1 | 5/1999 |
| WO | WO 2007/051959 A1 | 5/2007 |

OTHER PUBLICATIONS

GE Silicones, "Material Safety Data Sheet RTV615 A+B—kit (51-4.54kg)", retrieved from http://www.mgchemicals.com/msds/english/rtv/RTV615a.pdf, Jul. 22, 2005, 8 pages, GES Waterford Plant, 260 Hudson River Rd. Waterford, NY 12188 USA.
PCT International Search Report and Written Opinion of The International Searching Authority for related application No. PCT/US2010/026742, mailed Oct. 11, 2010, 9 pages.

* cited by examiner

*Primary Examiner* — J M Saint Surin
(74) *Attorney, Agent, or Firm* — Jayne C. Piana

(57) ABSTRACT

This invention relates to permanent, ultrasonic, flexible, dry-coupled, linear arrays for the inspection of pipelines, process equipment, and the like. The permanent, ultrasonic, flexible, dry-coupled, linear arrays detect and/or measure corrosion wall loss, stress corrosion cracking, and/or internal initiated pipeline cracking. The apparatus for ultrasonically testing materials includes a linear array of ultrasonic sensors, and a flexible, acoustically transmissive, dry-coupling surrounding at least a portion of each of the ultrasonic sensors.

11 Claims, 14 Drawing Sheets

DRY-COUPLED PERMANENTLY INSTALLED ULTRASONIC SENSOR LINEAR ARRAY

BACKGROUND

1. Field of the Invention

This invention relates to permanent, ultrasonic, flexible, dry-coupled, linear arrays for the inspection of pipelines, process equipment, and the like. The permanent, ultrasonic, flexible, dry-coupled, linear arrays detect and/or measure corrosion wall loss, stress corrosion cracking, and/or internal initiated pipeline cracking.

2. Discussion of Related Art

Conventional ultrasonic sensors have high manufacturing costs and have coupling issues or problems resulting in loss of signal or inaccurate readings. Good ultrasonic sound transmission depends upon removing all air between the sensor and a test surface. Sufficient readings and/or measurements involve the ultrasonic sensor transmitting and receiving a signal with minimal signal loss and/or degradation, such as without air bubbles and/or gaps. Ultrasonic sensors typically use a couplant to increase transmission between a test material and the sensor. Conventional liquid couplants include propylene glycol or glycerin. The liquid couplant dries, leaks, and/or runs out from the under the sensor which causes signal problems. Liquid couplants provide a temporary or short duration of suitable acoustic transmission. Cawley et al., International Patent Application Publication WO2007/051959 discloses an elongate strip of ultrasound transmissive material.

Attempts in the industry have been made to use magnets or adhesive bonding for ultrasonic energy transmission systems. However, these adhesive bonds have a high failure rate due to bond degradation and fracture over time. The energy input from the ultrasonic sensor may contribute to adhesive failure. Roarty, U.S. Pat. No. 4,881,409 discloses a flexible magnetic material with an array of ultrasonic transducers. Fripp et al., U.S. Pat. No. 7,234,519 discloses an adhesive bonding of transducers to pipe for oil drilling. While magnets or adhesive bonds may provide signal transmission for a longer duration than a liquid couplant before adhesive failure, there is still a need and a desire for ultrasonic sensors that can be installed for longer and/or permanent durations.

SUMMARY

These and other aspects of this invention are met at least in part by an apparatus and a method of testing materials with a dry-coupled permanently installed ultrasonic sensor linear array.

According to one embodiment, this invention relates an apparatus for ultrasonically testing materials. The apparatus includes a linear array of ultrasonic sensors, and a flexible, acoustically transmissive, dry-coupling surrounding at least a portion of each of the ultrasonic sensors.

According to one embodiment, this invention relates a method of testing materials. The method includes conforming a dry-coupling to a test material, securing the dry-coupling to the test material, and disposing a linear array of ultrasonic sensors with respect to the dry-coupling. The method includes measuring or detecting at least one property of the test material with the linear array through the acoustically transmissive dry-coupling.

BRIEF DESCRIPTION OF THE FIGURES

The above and other features and aspects of this invention are better understood from the following detailed description taken in view of the drawings wherein.

DETAILED DESCRIPTION

Figure 1:
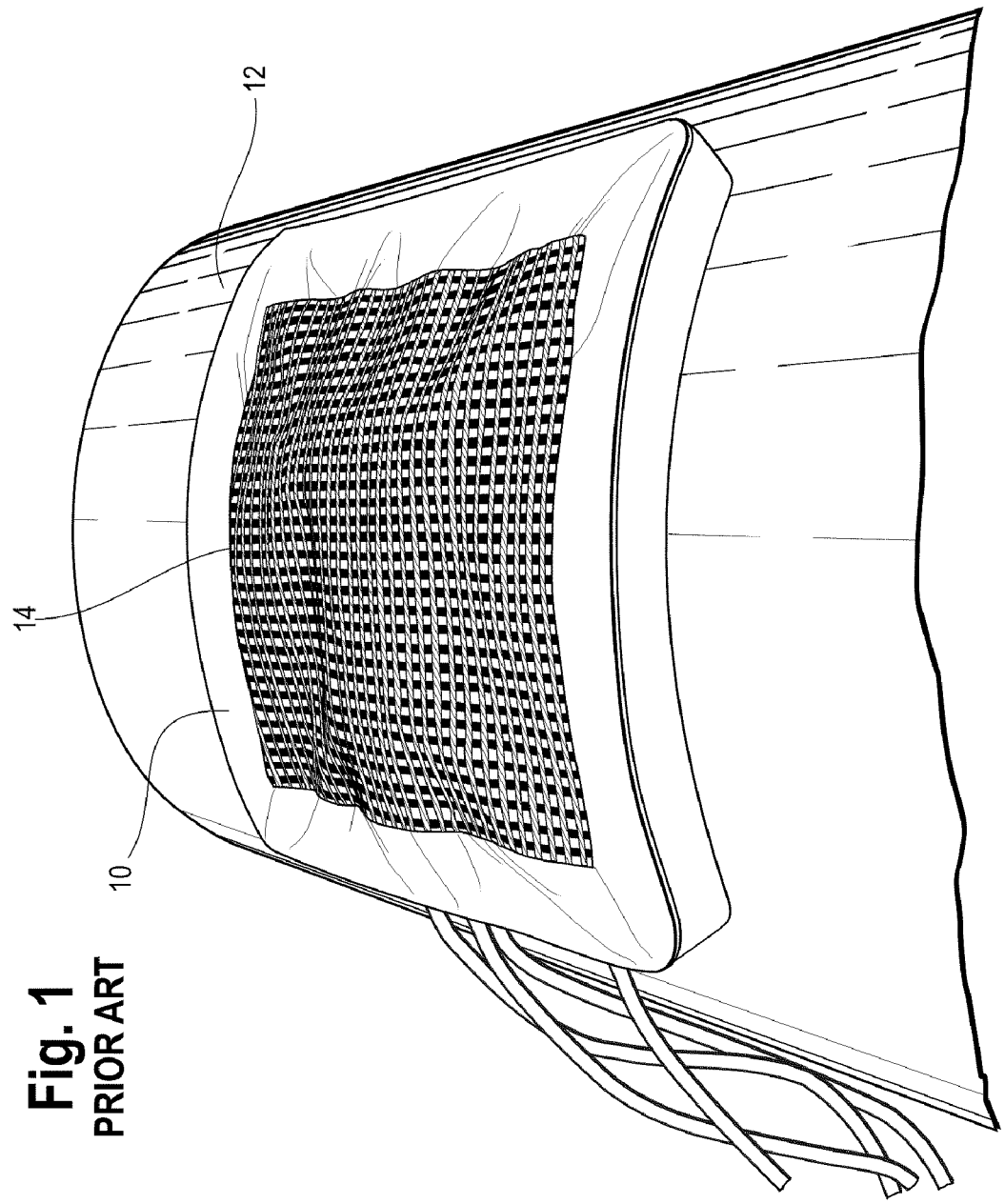
FIG. 1 shows a square vacuum coupled ultrasonic sensor array.

Ultrasonic thickness measurement and flaw detection may provide an important non-destructive testing method to allow safe and reliable operations of pipelines, oilfield equipment, refineries, chemical processing plants and/or any other suitable manufacturing or transportation system. Permanently installed ultrasonic sensors can be for continuous and/or periodic measurement of equipment wear and/or damage.

The ultrasonic devices of this invention may include a dry-coupling, such as without application of propylene glycol and/or glycerin. According to one embodiment, a dry-coupling includes an acoustically transmissive, conformable, semi-solid material to provide a substrate for the sensors and the associated wiring. Suitable dry-coupling materials include polymers, elastomers, plastormers, silicon-based materials, and/or any other relatively flexible substance. According to one embodiment, RTV 615 by Momentive Performance Materials (Wilton, Conn. USA) formerly GE Advanced Materials, may be used to form the dry-coupling. Desirably, the dry-coupling includes an ultrasonically conductive material that at least substantially conforms to a test surface, while providing ultrasonic transmission and/or reception without an additional couplant and/or an adhesive. The dry-coupling desirably does not degrade and/or fail over time due to input of ultrasonic energy.

Desirably, the permanent installation of the sensor arrays of this invention may allow for scanning of equipment with reduced contract services, reduced scaffolding, improved safety, improved integrity, and the like. For example, a pipe elbow located about 20 feet (6 meters) above the ground in a pipe rack would necessitate scaffolding to be set and block access to the operating unit. The technician would then climb the scaffold to take the measurements with a portable temporary ultrasonic (UT) unit, perhaps on a daily basis. In contrast, the permanent installed linear array of this invention could be placed on the elbow once and connected to a display at ground level and/or in the control house. The linear array could scan the elbow daily and/or more frequently without the expense and risk of a technician daily climbing a scaffold. Additionally, since the linear array is permanent, the scaffold can be completely removed and no longer block access to the operating unit, for example.

According to one embodiment, array manufacturing costs can be significantly reduced by utilizing an injection mold and vacuum heater curing process to form the dry-coupling. Arrays broadly include more than one item arranged in an order, such as a grid. Grids may include any suitable size and/or shape. Linear broadly includes items having a substantially longer length than a width, such as an array of 32×1 (rows×columns), 1×32 (row×columns), 2×64, and the like.

Array elements may be individually laid up or positioned before being bonded or fixed into the array, such as to simultaneously set and encapsulate 64 sensors at their correct incident angles through the preset shape of the injection mold. According to one embodiment, suitable manufacturing methods include injection molded arrays with preset incident angles. In the alternative, an individual sensor lay up process can be used to fabricate the array. Individual molds can be manufactured for each ultrasonic inspection modes used in ultrasonic corrosion and/or crack monitoring. The modes for the array may include: zero-degree thickness, angle beam shear wave, and/or time-of-flight diffraction (TOFD or sometimes referred to as TOF).

According to one embodiment, the ultrasonic device of this invention reduces the overall manufacturing and electronics requirements, such as rather than having 32 transmitting elements corresponding to 32 receiving elements in an array, a single long element covers a length of the receiving elements. Desirably, but not necessarily, the single long element pulses corresponding to each receiving element, such as about 32 times. A number of transmitting channels and associated cabling can be significantly reduced, such as by about 50%.

The ultrasonic device of this invention may operate in any suitable mode, such as using ultrasonic time of flight diffraction (TOFD) with 32 receiving elements and one transmitting ribbon piezoelectric element. The sensor can be formed by placing the elements in a mold having the necessary ultrasonic incident angles for TOFD.

According to one embodiment, the ultrasonic device of this invention may operate using ultrasonic (UT) zero degree and/or UT shear wave modes. Desirably, the dry-coupling includes a stationary location and/or a fixed position, such as without the ability to roll and/or travel down a length of pipe with a wheel or other mobile arrangement. The mechanisms affecting the test material may include pitting, wall loss, under deposit corrosion, under insulation corrosion, stress corrosion cracking, environmental cracking, cracking in the heat or weld affected zone or area, fatigue cracking, hydrogen induced cracking, chloride cracking, hydrogen embrittlement, caustic embrittlement, and any other manner of loss, degradation, and/or failure. The device may include the capabilities to monitor a change in size and/or growth of a crack.

The ultrasonic device of this invention may operate at any suitable temperature, such as between about ambient conditions and about 100 degrees Celsius. Desirably, the ultrasonic device may operate in winter temperatures, such as to −40 degrees Celsius. In the alternative, the ultrasonic device may operate with exposure to cryogenic conditions. Even more desirably, the ultrasonic device may operate at elevated temperatures, such as about 200-400 degrees Celsius. Low temperature operation may use and/or include one or more heat sources, such as resistance heaters or steam tracing. High temperature operation may use and/or include one or more heat sinks, such as fans or cooling lines. Usually, but not necessarily, an operating temperature of the ultrasonic device may be limited by the operating range of the dry-coupling.

Optionally, a box, a cover, a shield, a housing, and/or other suitable device may be placed over at least a portion of the apparatus of this invention, such as to protect and/or prevent damage from precipitation, temperature, ambient conditions, sunlight, ultraviolet radiation, dust, debris, and/or any other contaminant or damaging environment. According to one embodiment, the system of this device utilizes battery power and/or solar power sources (self-contained) and/or wireless (radio frequency) transmission for communication, such as to facilitate installation in remote locations without providing separate power and/or signal wires. Desirably, the device includes suitable electrical hardware for compliance with various classifications and/or divisions of the National Electric Code. The device may be intrinsically safe or non-spark-producing.

According to one embodiment, this invention includes ultrasonic flexible dry-coupled linear arrays for the inspection of pipelines to detect and/or measure corrosion wall loss, stress corrosion cracking (SCC) in welds, and internal diameter (ID) initiated cracking. Desirably, the arrays can be permanently mounted for an extended period of monitoring at temperatures of up to about 200 degrees Celsius.

According to one embodiment, a geometry and/or ultrasonic characteristics of the flexible dry-coupled array can be designed and fabricated to meet specific inspection requirements. For example, the array may be used to inspect pipes with a linear array applied generally longitudinally with respect to a length of the pipe, such as downstream of a high-pressure drop control valve causing cavitation. In the alternative, the linear array may be applied circumferentially with respect to a diameter of the pipe, such as downstream of an elbow subject to erosion. One useful application includes permanently mounting the linear array to a high velocity piping system for continuous and/or periodic monitoring, such as corrosion wall loss, SCC, and/or ID initiated cracking. The array elements can be at fixed locations, so the inspection results may be displayed as ultrasonic and/or C-scan images, such as used to compare wall thickness with respect to time.

The sensor array may periodically monitor a location and upon determining a change in parameters may increase the scanning to an increased frequency. For example, the array weekly measures wall loss but upon reaching a set thickness or a rate of loss between measurements, the array measures wall loss daily. The array may also be connected to or trigger an alarm and/or an alert, such as before reaching a critical wall thickness.

The array of sensors may output or be connected with a display, a printer, a storage device, a computer, a networked computer, and/or any other suitable device for receiving, storing, processing, forwarding and/or exchanging data.

The linear array of this invention can be fabricated into at least three different configurations: 1) 0 degree array for detection and measurement of thickness or corrosion wall loss, 2) TOFD array for SCC in welds, and 3) 45-degree shear wave array for ID initiated cracking. Other configurations are within the scope of this invention, such as a combination of 0 degree elements and 45-degree elements in the same linear array.

As used herein the terms "having", "comprising", and "including" are open and inclusive expressions. Alternately, the term "consisting" is a closed and exclusive expression. Should any ambiguity exist in construing any term in the claims or the specification, the intent of the drafter is toward open and inclusive expressions.

Regarding an order, number, sequence and/or limit of repetition for steps in a method or process, the drafter intends no implied order, number, sequence and/or limit of repetition for the steps to the scope of the invention, unless explicitly provided.

According to one embodiment, the invention includes an apparatus for ultrasonically testing materials. Ultrasound broadly includes a cyclic sound pressure with a frequency greater than an upper limit of human hearing, such as about 20 kilohertz (2 megahertz or 20,000 hertz). The ultrasonic transmitters and/or receivers of this invention may operate at any suitable frequency, such as about 20 kilohertz, 40 kilohertz, 50 kilohertz, 60 kilohertz, 80 kilohertz, 100 kilohertz, and/or any other relatively high frequency.

Suitable materials for testing broadly include metals, steels, mild steels, stainless steels, alloys, ceramics, glasses, plastics, thermoplastics, thermosets, and/or any other material that may have latent and/or patent defects or flaws. The test materials may be tested during fabrication, after construction, while in operation, during a shutdown and/or any other suitable time. The test material may be in any suitable service, such as pipelines, oil fields, deepwater oil extraction systems, sub-sea drilling operations, tar sands processing units, oil refineries, chemical plants, transportation systems, nuclear plants, utility plants, and/or any other processes or uses.

The apparatus may include a linear array of ultrasonic sensors, and a flexible, acoustically, transmissive, dry-coupling surrounding at least a portion of each of the ultrasonic sensors of the linear array. The linear array may include any suitable dimensions, such as a length greater than about twice a width, a length greater than about four times a width, a length greater than about ten times a width, a length greater than about thirty times a width, a length greater than about fifty times a width, a length greater then about one hundred times a width, and/or any desirable multiple of length and/or width. Surrounding may include embedding, encasing, encapsulating, covering, and/or any other suitable arrangement.

According to one embodiment ultrasonic sensors may include any suitable device and/or tool for generating, transmitting and/or making an ultrasonic signal and/or pulse. Ultrasonic sensors may include any suitable device and/or tool for receiving, sensing, and/or detecting an ultrasonic signal and/or pulse. Ultrasonic sensors may include both sending and/or receiving capabilities in the same unit.

The ultrasonic sensors may mount at any suitable angle, such as with respect to a surface of the test material. According to one embodiment, each ultrasonic sensor mounts at an angle of incidence relative to a test material surface of about −90 degrees to about +90 degrees, such as from full contact in one direction to full contact in an opposite direction. In the alternative, each ultrasonic sensor mounts at an angle of incidence relative to a test material surface at and/or about 0 degrees and/or about 45 degrees. Other angles of incidence are possible without departing from the scope of this invention.

Desirably, but not necessarily, the sensors may mount and/or be placed in a generally parallel alignment, such as each sensor having about the same orientation from front to back. In the alternative the sensors may mount and/or be placed at any suitable angle with respect to each other, such as at about 45 degrees from each adjacent sensor, at about 90 degrees from each adjacent sensor and/or any other arrangement.

The linear array may include any suitable number of sensors for sending and/or transmitting, such as about 10 sending and about 10 receiving, about 32 sending and about 32 receiving, about 1 sending and about 32 receiving, about 64 sending and about 128 receiving, and/or any other suitable combination. Parallel and/or series configurations are possible.

According to one embodiment, multiple banks and/or clusters of sensors may be arranged in a daisy chain configuration. In the alternative, an array of hubs may combine, such as with one or more hubs to form an array of arrays. The use of multiplexing and/or other mechanisms to increase bandwidth and/or reduce wiring is possible. Desirably, the linear array includes at least about 2 ultrasonic sensors, at least about 32 ultrasonic sensors, at least about 64 sensors, and/or at least about 1024 sensors.

The sensors may include any suitable size and/or shape, such as about 3 millimeters to about 6 millimeters, about 13 millimeters, about 25 millimeters, and/or any other useful dimension. Desirably, but not necessarily, a sensor size may at least partially correspond to a radius of curvature of the test material or substance, such as a smaller radius may use a smaller sensor and a larger radius may use a larger sensor, for example.

The apparatus may include any suitable number of liner arrays. Desirably a first linear array transmits and a second linear array receives the ultrasonic signal. In the alternative, the second linear array transmits and the first linear array receives. The first and the second array may include both transmitting and/or receiving capabilities (two-way). The second linear array may be in the same or different dry-coupling as the first linear array. In the alternative the first linear array and/or the second linear array includes a single elongated sensor or transmitter. According to one embodiment, the first linear array includes a strip sensor and the second linear array includes a plurality of sensors. The linear arrays may have any suitable orientation and/or relationship with respect to each other, such as at least generally parallel with respect to one another.

The dry-coupling may include any suitable material, such as a semi-solid polymeric material, a polysilicone, a polyimide and/or any other suitable material. According to one embodiment, the dry-coupling of this invention excludes one or more of magnets, vacuum, adhesives, and/or liquid coupling agents.

According to one embodiment, the ultrasonic sensors include a zero-degree thickness configuration, an angle beam configuration, and/or a time-of-flight diffraction configuration. Other configurations and/or combinations are within the scope of this invention.

According to one embodiment, the apparatus may include a rigid material between or disposed with respect to at least one ultrasonic sensor and a contact surface of the dry-coupling, such as a signal travels through the rigid material, through a portion of the dry-coupling and into the test material. Optionally, at least a portion of the dry-coupling also is positioned and/or disposed between the sensor and the rigid material. Desirably, the rigid material includes high ultrasonically transmissive substances, such as poly(methyl methacrylate) and/or any other suitable stiff material.

The rigid material may include any suitable size and/or shape, such as a wedge, a piece of pie, a block, a cube, and/or any other geometry. A wedge may include any suitable substantially triangular cross-section shape and have any suitable angle, such as about from 10 degrees to about 80 degrees, and desirably about 45 degrees.

A high temperature application (about 200 degrees Celsius to about 400 degrees Celsius) embodiment may include dry-coupling materials for the increased temperatures, such as polyimides and/or other suitable materials. In the alternative, a metallic ultrasonic point measurement dry-coupled probe may be used for high temperatures. Desirably, the metal dry-coupling includes flexible materials, such as foils and the like. In the alternative the metal coupling includes soft and/or malleable metals and/or alloys for sufficient UT transmission. Composite materials or laminate materials, such as metal coated Mylar® from E. I. du Pont de Nemours and Company (Wilmington, Del. USA), are also within the scope of this invention for the apparatus.

According to one embodiment, an impedance matching paint layer may improve a surface condition of a test material. Ultrasonic beam expansion such as for the 45-degree shear array, may be accomplished by lowing the frequency. Paint differs from other liquid couplants in that is it inherent to the pipe, that is becomes a part of the pipe. Desirably, the lower frequency results in a wavelength that is about half the length of a UT signal. In the alternative, shortening a chip height may also shorten the near field and result in an expanded beam.

According to one embodiment, the invention includes a method of testing materials. The method may include conforming a dry-coupling to a test material. Conforming includes broadly at least generally and/or substantially bending and/or shaping at least a portion of the dry-coupling with respect to and/or around at least a portion of the test material. Desirably, the step of conforming may include imparting shape retaining properties to the dry-coupling, such as in at least a general form of the test material and/or specimen. The dry-coupling may include shape retaining elements, such as relatively thin metal strips embedded within the dry-coupling for shape and/or form holding characteristics.

The method may include securing the dry-coupling to the test material. Securing includes broadly any suitable action to attach, affix, anchor, join and/or mount at least a portion of the dry-coupling with respect to at least a portion of the test material. According to one embodiment, the securing may occur or be completed by any suitable mounting device, such as a zip tie, a cable tie, a band clamp, a radiator clamp, a worm gear clamp, a clamp and bolt arrangement, and/or any other apparatus to hold the dry-coupling with respect to the test material.

Desirably, the securing allows permanent mounting of the dry-coupling. Permanent differs from temporary, as used herein. Temporary mountings, such as with liquid couplants and held in place by a users hand and/or bungee cords may last for a few minutes to at most a couple of hours. In contrast, permanent mounting may last for a minimum of seven days, desirably at least a month, at least a year, more desirably at least 3 years, at least 5 years, and/or any other suitable duration. Also desirably, the securing device, the dry-coupling and/or the sensors have at least the same and/or similar useful service life.

The method may include securing a linear array of ultrasonic sensors with respect to the dry-coupling. The securing the linear array of ultrasonic sensors may include encapsulating, gluing, adhering, disposing with respect to, and/or any other suitable step to combine at least a portion of the sensor with the dry-coupling. Desirably, but not necessarily, the dry-coupling surrounds at least a portion of each sensor without an additional adhesive.

The method may include measuring or detecting at least one property of the test material with the linear array through the acoustically transmissive dry-coupling. The at least one property may include wall thickness, pitting, crack detection, crack size, change in crack size, growth of crack, material composition, material density, material integrity, thickness of deposit, thickness of scale, speed of sound in the material, and/or any other suitable parameter and/or quantity. Desirably, the step of measuring includes detecting wall loss and/or detecting cracking. In the alternative, the step of measuring may include a zero-degree thickness operation, an angle beam operation, and/or a time-of-flight diffraction operation.

The measuring may include transmitting a signal to the linear array from a second generally parallel linear array, for example.

According to one embodiment, the step of securing the linear array may include ultrasonically coupling the linear array with the test material, such as without magnets, vacuum, adhesives, and/or liquid coupling agents. Desirably, the step of securing the dry-coupling to the test material includes permanently affixing the linear array to the test material. The securing the dry-coupling may last for at least about 6 months without requiring resecuring or repositioning, the securing the dry-coupling may last for at least about 3 years without requiring resecuring or repositioning, and/or the securing the dry-coupling may last for any other suitable duration that is longer than a temporary connection.

The method may include preparing and/or applying to a surface of the test material an acoustically transmissive treatment. The acoustically transmissive treatment may include any suitable material and/or application, such as a paint or a tape with a sufficient ultrasonic transmission characteristic. Tape includes an adhesive to attach the ultrasonic transmitting material to the test surface and differs from adhesive couplings described above, since there is no adhesive securing the sensor or array to the tape.

Surface preparation including acid washing, descaling, caustic washing, sanding, sand blasting, shot blasting and/or any other suitable procedure may be performed prior to securing the linear array and/or the transmissive treatment. In the alternative, the method of testing the material may exclude surface preparation and/or acoustically transmissive treatment, where the dry-coupling mates with the surface of the test material with sufficient ultrasonic transmission characteristics.

The method may include transmitting from the second generally parallel linear array by sending a signal corresponding to each of the ultrasonic transducers from a single elongated transmitting sensor, for example.

EXAMPLES

The linear array of this invention was fabricated into three prototypes: 1) 0 degree array for detection and measurement of corrosion wall loss, 2) TOFD array for SCC in welds, and 3) 45-degree shear wave array for I.D. initiated cracking.

Example 1

Prior Art

A known flexible ultrasonic array 10 has a square configuration of ultrasonic transducer elements vacuum attached to a pipe 12, as shown in FIG. 1. The array 10 of FIG. 1 included 1024 transducer elements 14 having 0.25 inch (6.35 mm)× 0.25 inch (6.35 mm) size and arranged in a 32×32 square element matrix. The array 10 was vacuum coupled to a 12 inch (30.5 cm) diameter pipe 12. The dimensions of the active area of the array 10 were 8 inches (20.3 cm) by 8 inches (20.3 cm) for a total inspection area of 64 square inches (162.6 cm squared). Vacuum couplings did not provide a permanent mounting solution and failed due to leakage and/or thermal cycling.

Example 2

0 Degree Wall Thickness Array

Figure 2:
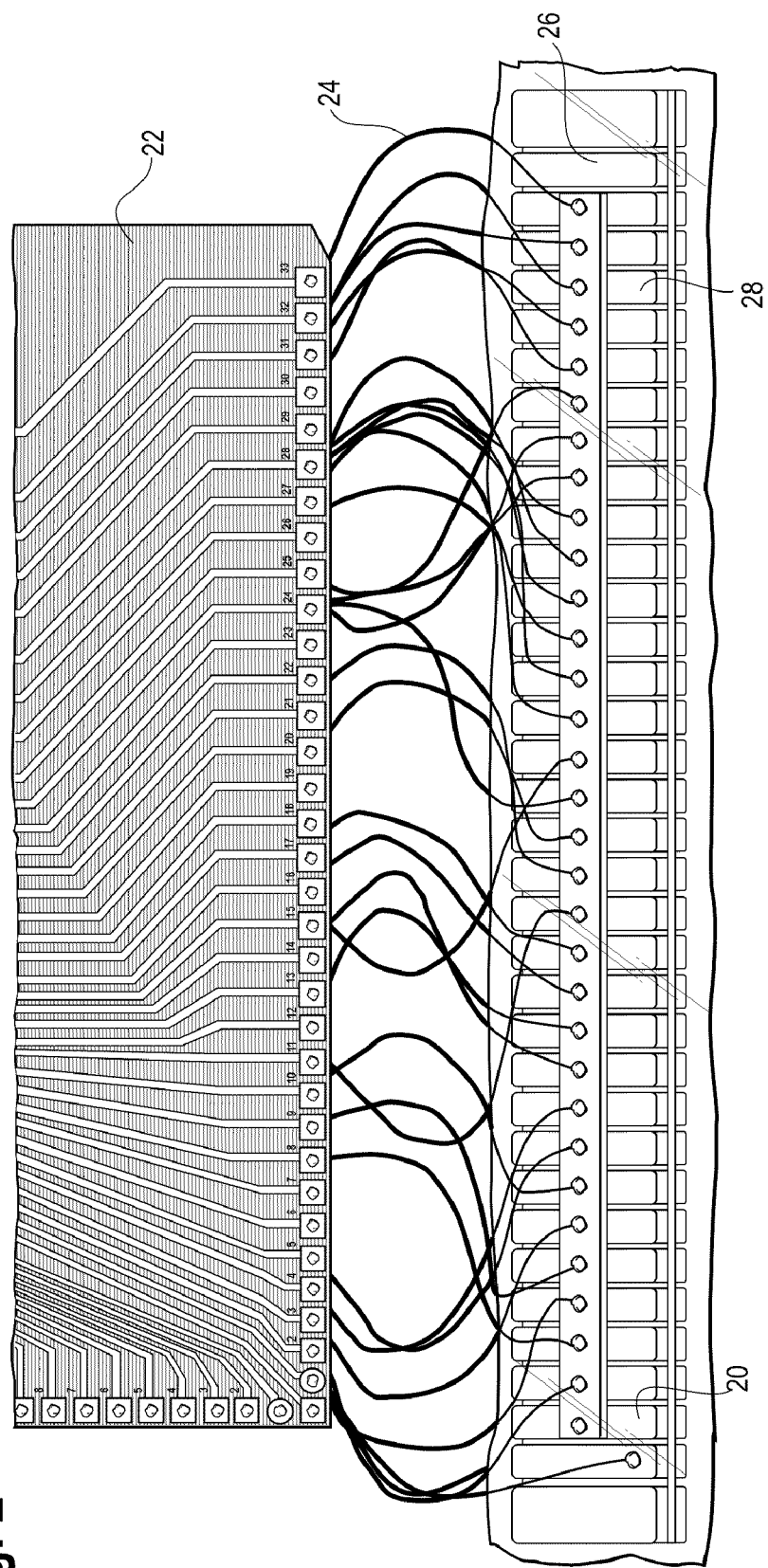
FIG. 2 shows a 0 degree wall thickness array, according to one embodiment.

As shown in FIG. 2, a first prototype was constructed in 0 (zero) degree (angle of incidence) configuration. The 0 degree linear array 20 was tested using a 32 channel Array Scanner (not shown) from HD Laboratories, Inc (Issaquah, Wash. USA) by attaching an 8 inch×8 inch (203 mm×203 mm) blanket circuit board 22 with wires 24. The scanner stores and/or places in memory all scanned data. The device could be configured to display any combination of the "A", "B-X", "B-Y", "C", and "C-TOF". Once the scan is stored, the gates were manipulated to study any portion of the scan. Tests were conducted with dry-coupled interfaces 26, where no wet couplants, adhesives and/or vacuum pressure were used to assist with ultrasonic transmission. The tests were performed at room temperature.

Figure 3:
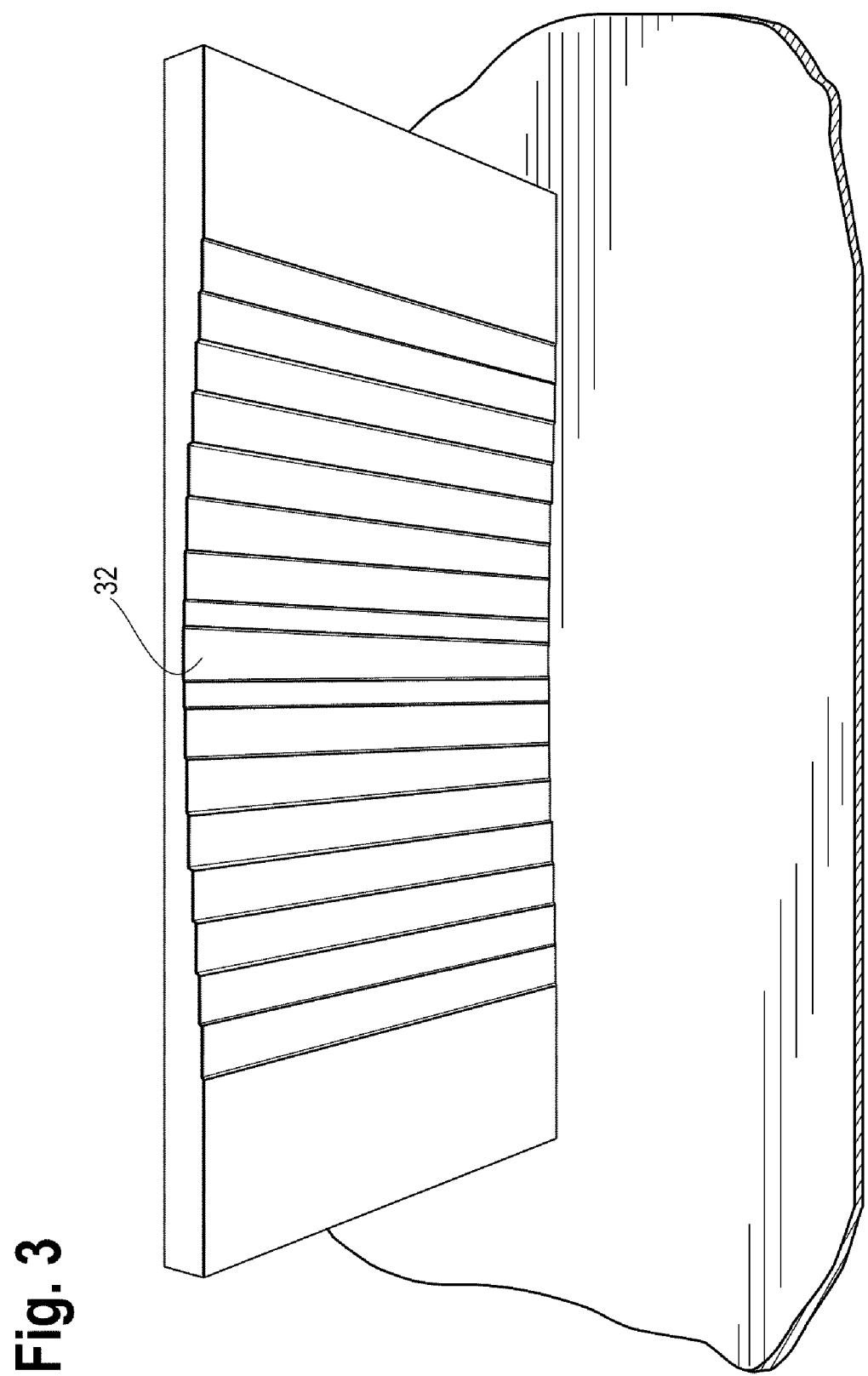
FIG. 3 shows a test block for wall thickness.
Figure 4:
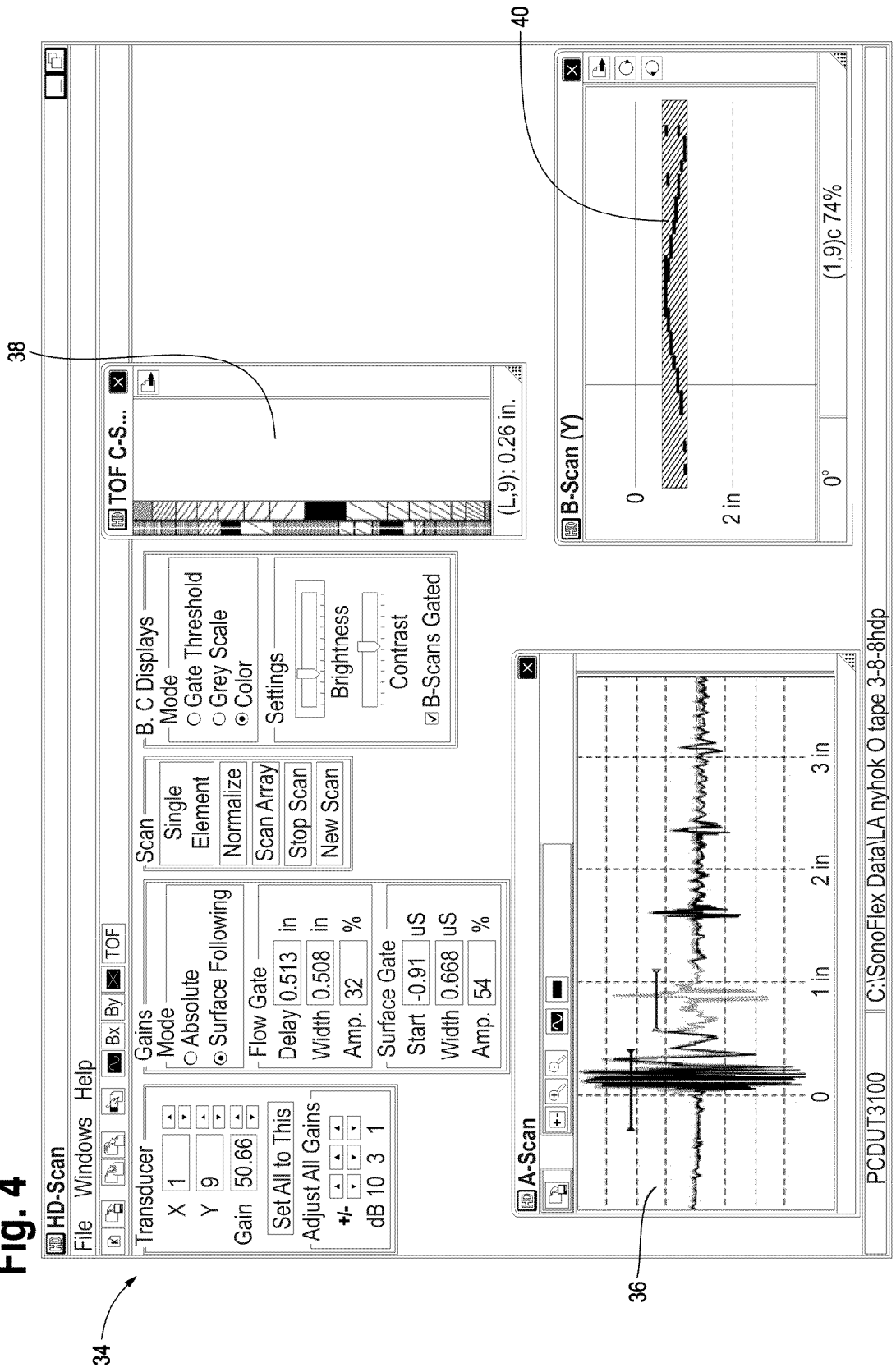
FIG. 4 shows a scan of the test block of FIG. 3, according to one embodiment.
Figure 6:
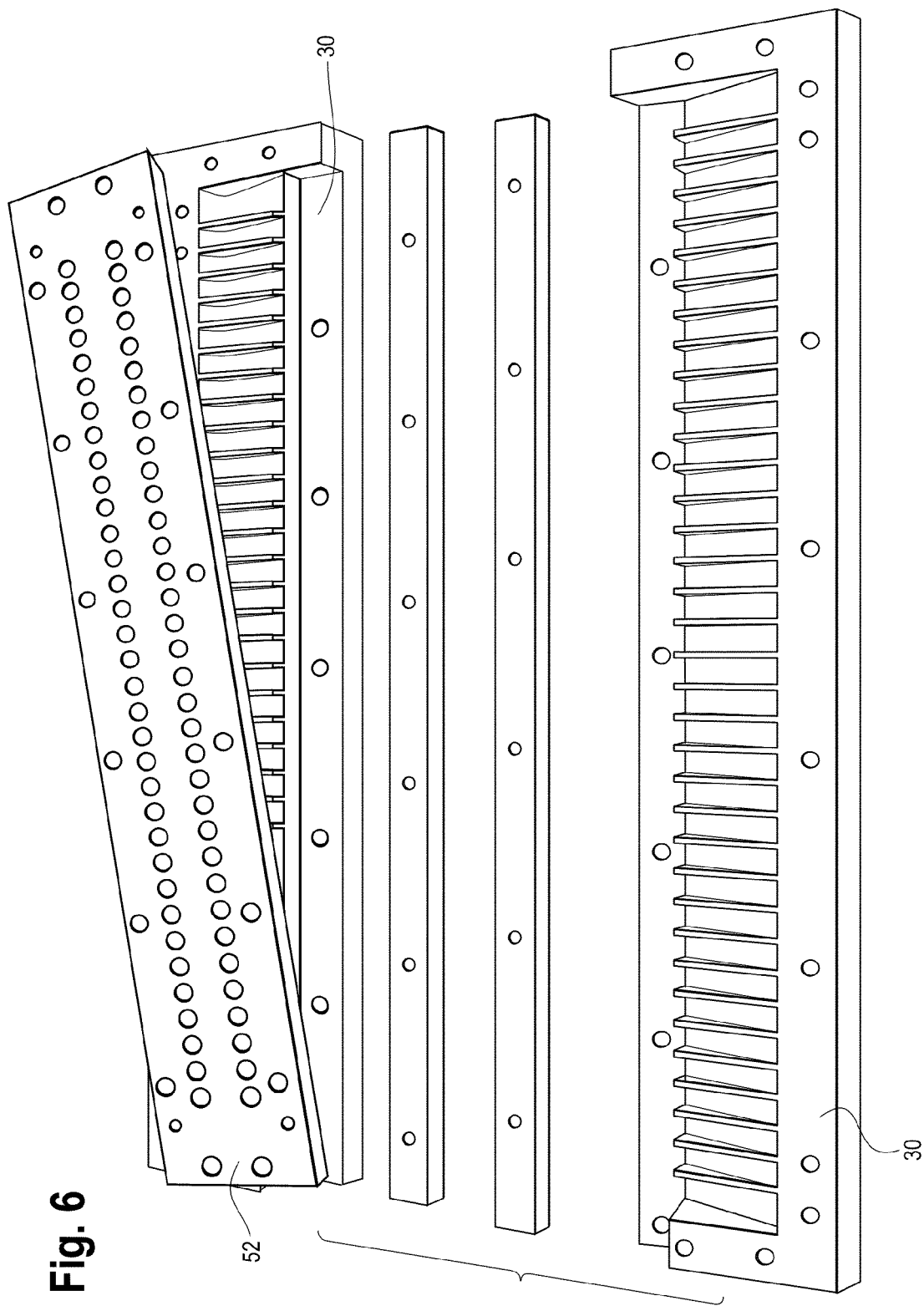
FIG. 6 shows molds and a chip alignment tool, according to one embodiment.

The linear array of this invention was fabricated with a 0 degree wall thickness configuration in FIG. 2. The 0 degree array 20 for sensing wall thickness included thirty-two 8 MHz ¼ inch (6.35 mm) diameter elements or sensors 28 mounted on a dry-coupling 26 of RTV 615 substrate. The dry-coupling 26 was segmented both top and bottom by joining the molds 30 as shown in FIG. 6 in a back to back arrangement. FIG. 3 shows a stepped thickness test block 32 of a one half-inch (12.7 mm) plate with 1/16th inch (1.58 mm) steps to a minimum thickness of 0.25 inches (6.35 mm) in the center. The results of scanning the thickness of the test block 32 are shown on the instrument display 34 in FIG. 4 including "A" scan 36, "C-TOF" scan 38, and the "B" scan 40 or sometimes referred to as a B-Y scan or y. The profile of the test block 32 is shown in the "B" scan 40. The 0 degree wall thickness array 20 successfully measured the thickness of the test block 32.

Example 3

TOFD Array

Figure 5:
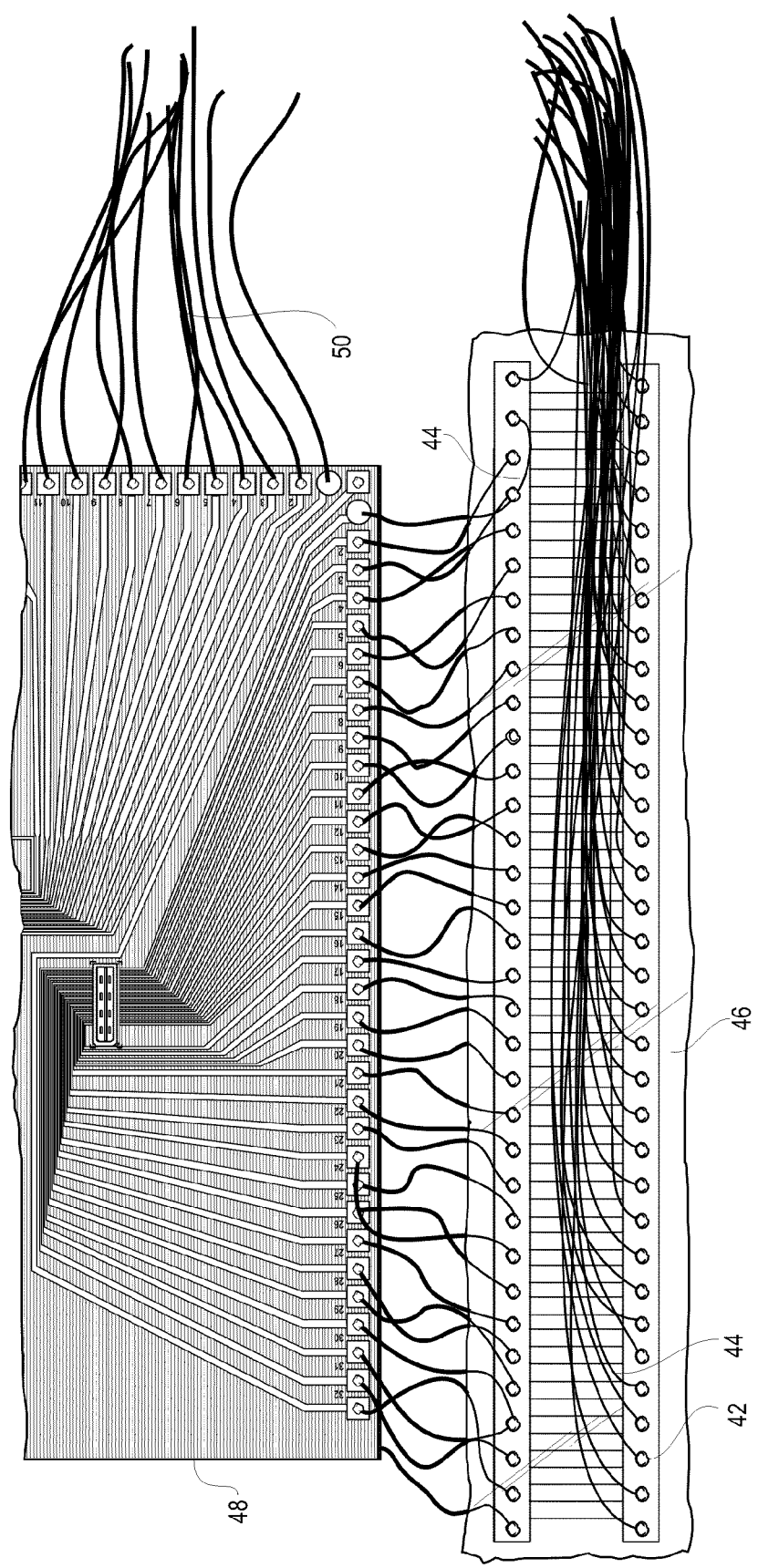
FIG. 5 shows a time of flight diffraction (TOFD) array, according to one embodiment.

A second prototype was constructed as above except configured to be a TOFD array 42 with thirty-two 8 MHz ¼ inch (6.35 mm) diameter elements or sensors 44 for both the transmitters and the receivers mounted on a dry-coupling 46 of RTV 615 segmented in a wedge strip, as shown in FIG. 5. The TOFD array 42 as shown in FIG. 5 is connected to an 8 inch x 8 inch (203 mm×203 mm) array circuit board 48 for testing with the scanner (not shown) with wires 50. The wedges were cast to the correct incident angle in molds. Due to the large sonic velocity difference between the RTV615 and the carbon steel, the mold angles were controlled to tight tolerances.

A chip mounting and a chip placement mold was designed and fabricated as shown in FIG. 6. FIG. 6 shows the molds 30, such as where the lower mold is typical of the segmented wedge molds 30. A chip alignment tool is shown at the top of FIG. 6.

Figure 7:
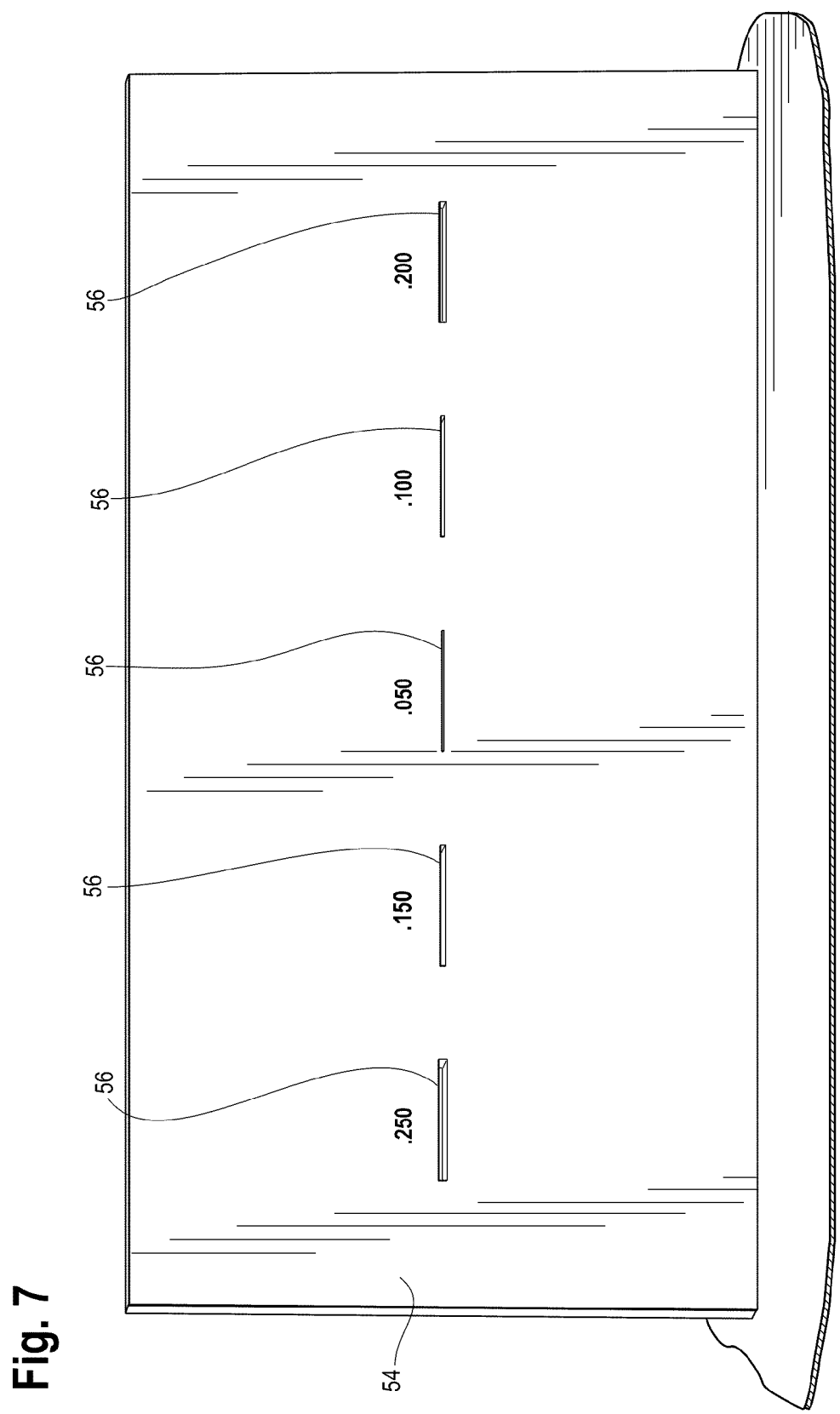
FIG. 7 shows a test block for crack detection.
Figure 8:
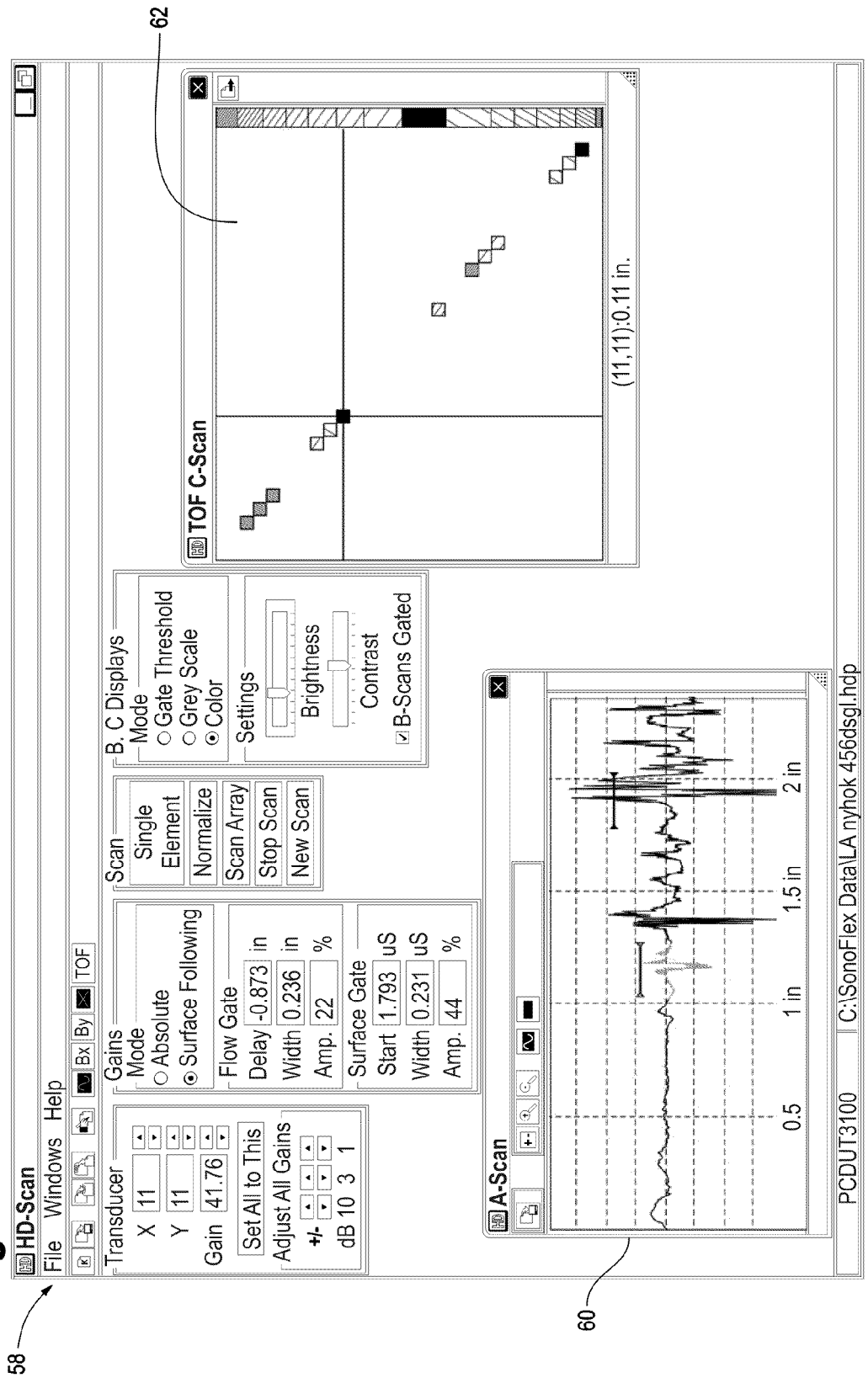
FIG. 8 shows a scan of the test block of FIG. 7, according to one embodiment.

FIG. 7 shows a notched test block 54 with a series of cracks or notches 56 to simulate SCC. The notches 56 measured from left to right: 0.250 inches (6.35 mm); 0.150 inches (3.81 mm); 0.050 inches (1.27 mm); 0.100 inches (2.54 mm); and 0.200 inches (5.1 mm), respectively. FIG. 8 shows the instrument display 58 with the results of successfully detecting the notches 56 form the test block 54 with the TOFD array 42 including the "A" scan 60, and "C-TOF" scan 62. The notches 56 in the test block 54 appear as variations relating to depth in the "C-TOF" scan 62 or display.

Example 4

45 Degree Shear Wave Array

Figure 9:
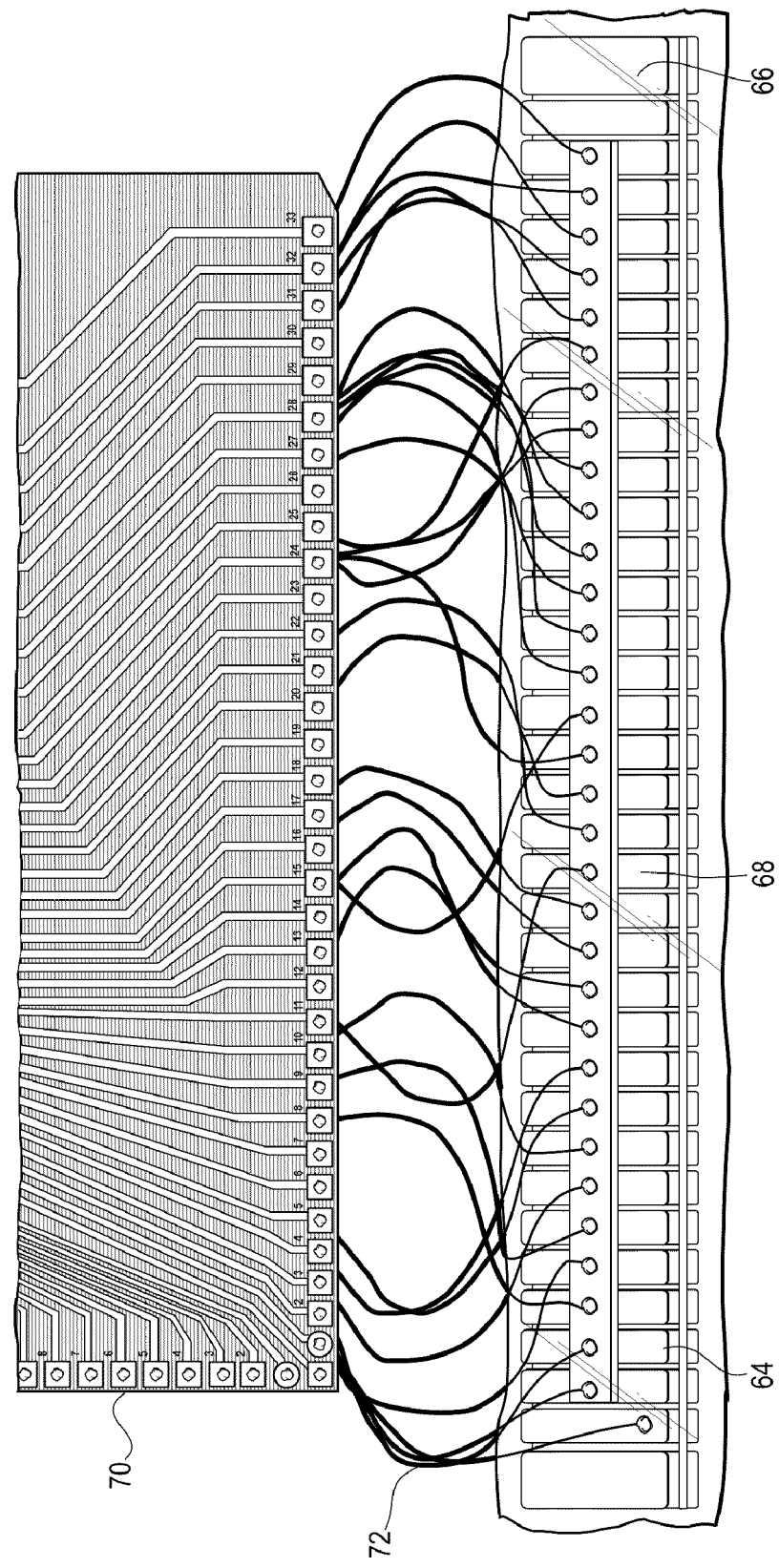
FIG. 9 shows a shear wave array, according to one embodiment.

A third prototype was constructed in a 45-degree shear wave array 64. The array 64 included thirty-two 8 MHz ¼ inch (6.35 mm) diameter sensors 68 or elements, mounted on a dry-coupling 66 of RTV 615 segmented in a wedge strip, as shown in FIG. 9. The wedges were cast to the correct incident angle in molds 30. As with the TOFD array 42, the mold angles were controlled to tight tolerances in the shear wave array 64. The molds 30 for the array 64 are shown in FIG. 6. The sensors 68 were connected to the circuit board 70 with wires 72.

Figure 10:
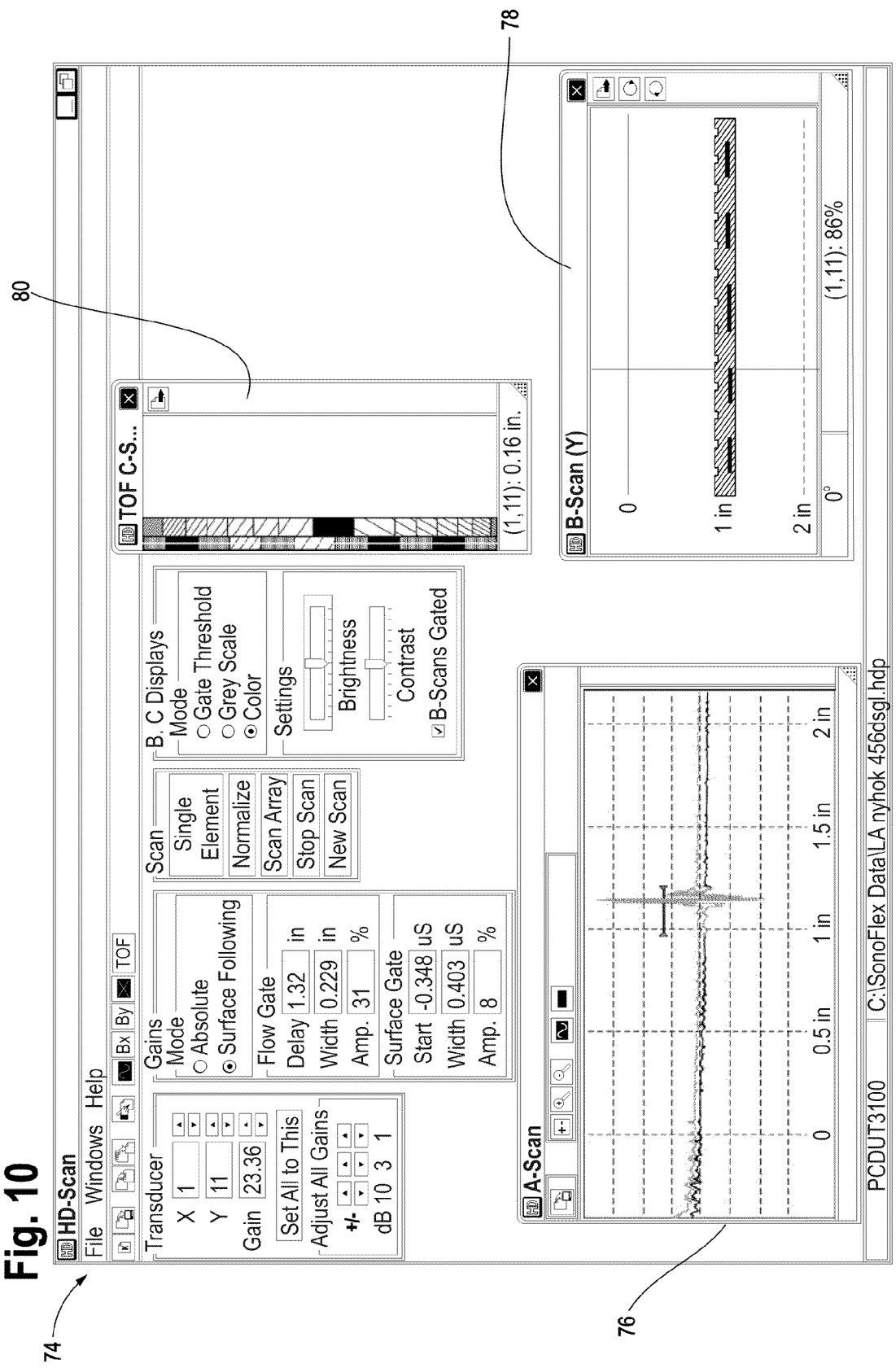
FIG. 10 shows a scan of the test block of FIG. 7, according to one embodiment.

For testing the 45-degree array 64 was used for detection of the notches 56 of the notched test block 54 in FIG. 7. All the notches 56 were seen as corner traps and appear the same in spite of size differences. Further development to expand the beam will result in improved tip diffraction monitoring and aid in crack size determination. The results of scanning the notched test block 54 are shown in FIG. 10. FIG. 10 shows an instrument display 74 with an "A" scan 76, a "B" scan 78, and a "C-TOF" scan 80. The notch plate corner reflectors can be seen in the "B" scan 78, while the "TOF-C" scans 80 are the same indicating a common depth.

The results of the prototype flexible arrays of Examples 1-4 for pipeline inspection successfully measured and/or detected the characteristics of the test materials. The flexible dry-coupling made from RTV 615 provided sufficient acoustic transmission without the issues of liquid couplants (manual scanning) and/or adhesive bonding. The beam size in the 45-degree shear array could be expanded to avoid being too collimated, such as making it difficult to get sufficient tip diffraction signals. Nonetheless the corner trap detection was excellent. The flexible linear array worked well as tested on the calibration blocks.

The RTV615 as a dry couplant refracting wedge provided sufficient UT coupling, but a reflection coefficient from the RTV615 to steel may be high, such as about 95%. According to one embodiment, this invention may include an additional material layer and/or matching layer to the coupling, such as having a geometric mean, for example, of about 6.5 Rayles and/or any other suitable value. The surface condition of the pipe can be a factor in successful operation. Adequate pipe preparation only improved the operation, such as with polyimide tape (Kapton® from E. I. du Pont de Nemours and Company, Wilmington, Del. USA). The Kapton® tape improved sonic velocity matching and appeared to overcome some surface imperfections. Sufficient pressure of the dry-coupling and the test material ensures good coupling. It has been found that if pressure is applied unevenly across the array, the refracted angle of the beam in the pipe wall may be affected.

Example 5

1×64 Ultrasonic Linear Array

Figure 11:
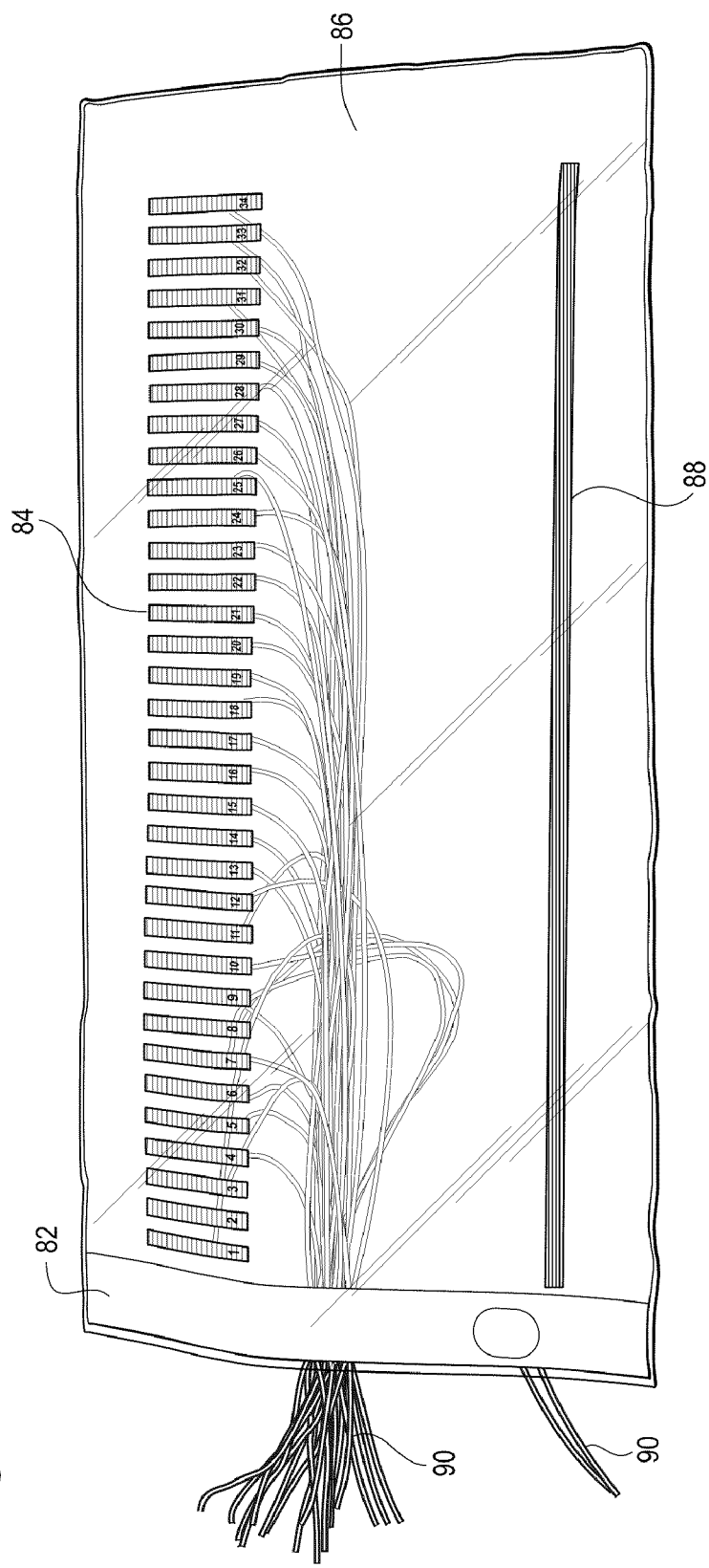
FIG. 11 shows a linear array with a single sending sensor, according to one embodiment.

As shown in FIG. 11, an ultrasonic flexible array 82 of 1×64 Ultrasonic sensors 84 was fabricated. The array included a surface compliant semi-solid substrate 86 which needed no conventional ultrasonic couplant (liquid). The linear array 82 was not affected by differences and variations of linear expansion between the array substrate 86 and test specimen, including growth. The array 82 withstood temperatures up to 200 degrees Celsius on a continuous basis.

The single transmitting sensor 88 reduces the number of transducers/channels by 50% versus configurations with a discrete sending sensor corresponding to a different discrete receiving sensor. The fabrication or lay-up mold (not shown) of the array was completed without angled wedges, which reduced lay-up time by 50%. The configurations included UT thickness measurement, UT shear wave, UT TOFD, and/or UT phased arrays for corresponding size pipe, pipe diameter or flat surfaces. Wires 90 connect the sensors 84 and transmitting senor 88 to an instrument display (not shown).

Figure 12:
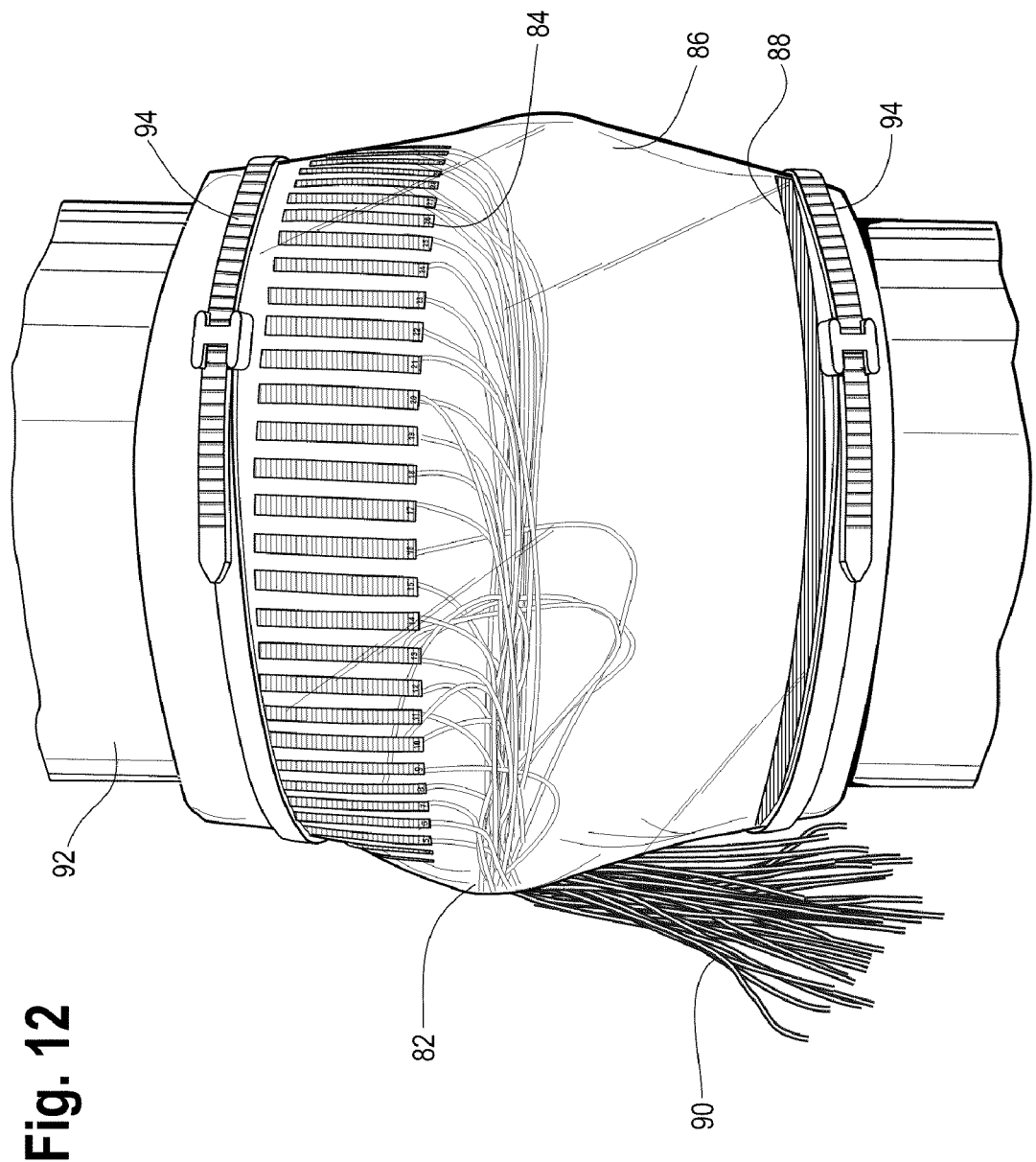
FIG. 12 shows the linear array of FIG. 11 installed on pipe, according to one embodiment.
Figure 13:
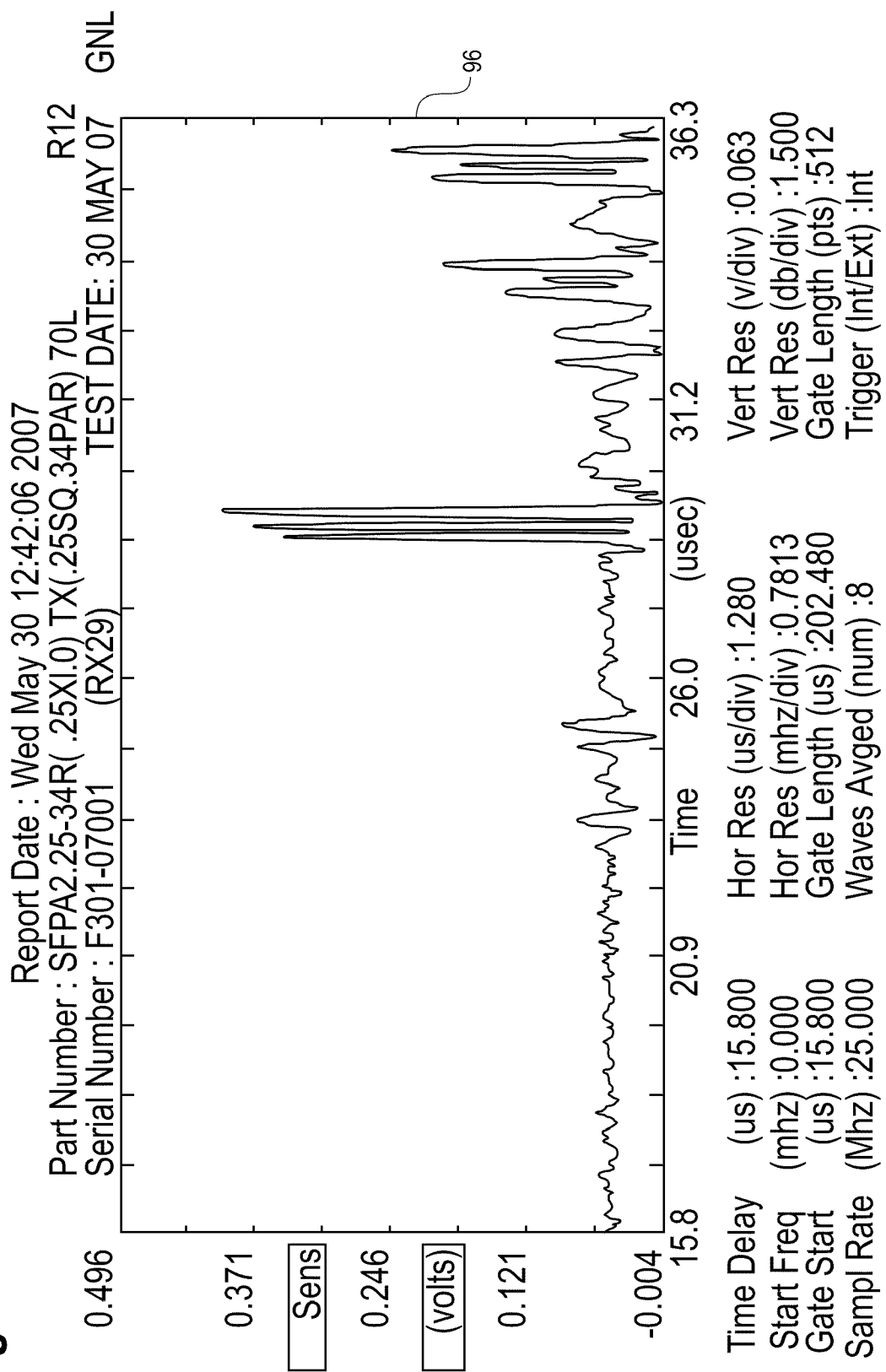
FIG. 13 shows a scan of the pipe of FIG. 12, according to one embodiment.

FIG. 12 shows the ultrasonic flexible array 82 of FIG. 11 installed and conformed on and to a pipe 92 by mounting devices 94 (zip ties). FIG. 13 shows the UT TOFD scan 96 from the UT sensor array 82 of FIGS. 11 and 12.

Example 6

Angles of Incidence

Figure 14:
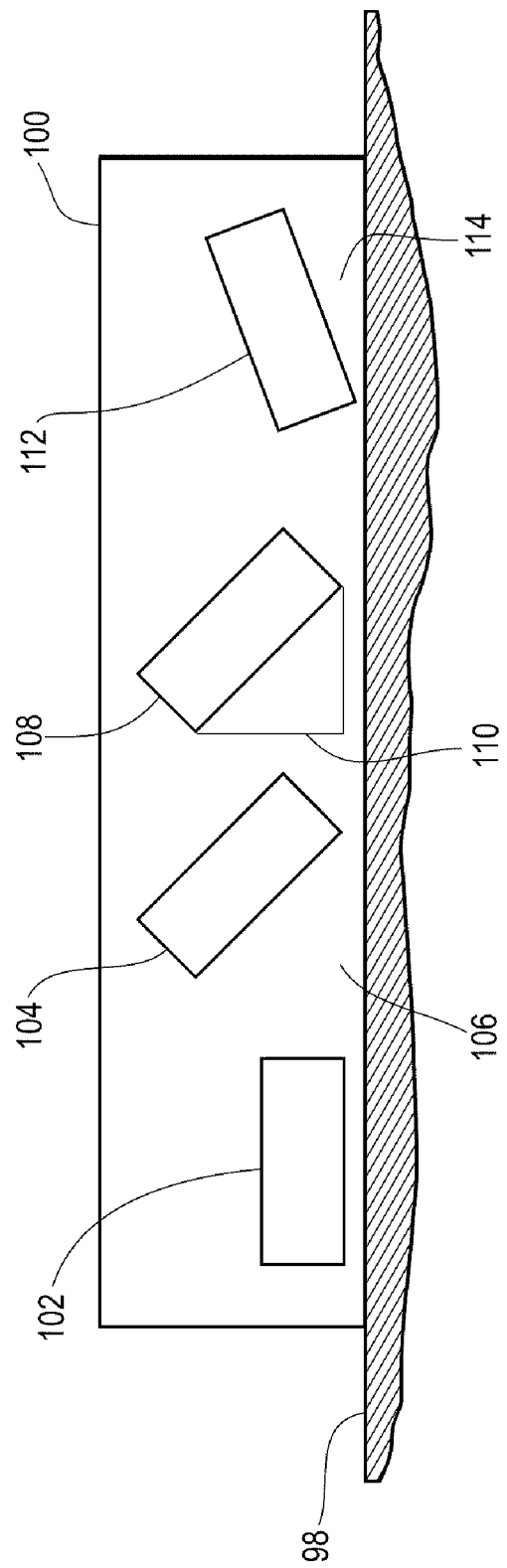
FIG. 14 shows a partial cross section of a linear array, according to one embodiment.

As shown in FIG. 14 and according to one embodiment, a test material 98 may be in contact with a dry-coupling 100. The dry-coupling 100 may include at least one 0 degree sensor 102 embedded within. The 0 degree sensor 102 may have a surface or alignment generally parallel with at least a portion of the test material surface, such as about a 0 (zero) degree angle of incidence with respect to the test material 90.

The dry-coupling 100 may include at least one 45 degree sensor 104 embedded within. The 45 degree sensor 104 may have a surface or alignment generally about 45 degrees from the test material surface and shown by angle 106 and excluding any other materials than the substrate of the dry-coupling 100. In the alternative, a second 45 degree sensor 108 may include a wedge 110, such as to improve ultrasonic transmission and/or reception. The dry-coupling 100 may include a fourth sensor 112 having a lesser angle 114, such as about −20 degrees. Angles can be positive and/or negative, for example.

While in the foregoing specification this invention has been described in relation to certain embodiments, and many details are set forth for purpose of illustration, it will be apparent to those skilled in the art that this invention is susceptible to additional embodiments and that certain of the details described in this specification and in the claims can be varied considerably without departing from the basic principles of this invention.

We claim:

1. A method of testing materials, the method comprising:
   conforming a dry-coupling to a test material;
   securing the dry-coupling to the test material;
   disposing a flexible linear array of ultrasonic sensors with respect to the dy-coupling; and
   measuring or detecting at least one property of the test material with the linear array through the acoustically transmissive dry-coupling, wherein the measuring comprises transmitting a signal to the linear array from a second generally parallel linear array.

2. The method of claim 1, wherein the securing the linear array comprises ultrasonically coupling the linear array with the test material without magnets, vacuum, adhesives, or liquid coupling agents.

3. The method of claim 1, wherein the securing the dry-coupling to the test material comprises permanently affixing the linear array to the test material.

4. The method of claim 1, further comprising preparing a surface of the test material with an acoustically transmissive treatment.

5. The method of claim 1, wherein the acoustically transmissive treatment comprises a paint or a tape.

6. The method of claim 1, wherein the measuring comprises one of the group consisting of detecting wall loss and detecting cracking.

7. The method of claim 1, wherein the measuring comprises one of the group consisting of a zero-degree thickness operation, an angle beam operation, and a time-of-flight diffraction operation.

8. The method of claim 1, wherein the transmitting from the second generally parallel linear array sends a signal corresponding to each of the ultrasonic transducers from a single elongated transmitting sensor.

9. The method of claim 1, wherein the securing the dry-coupling lasts for at least 6 months without requiring resecuring or repositioning.

10. The method of claim 1, wherein the securing the dry-coupling lasts for at least 3 years without requiring resecuring or repositioning.

11. The method of claim 1, wherein the conforming comprises imparting shape retaining properties to the dry-coupling.

* * * * *